(12) United States Patent
Dubach

(10) Patent No.: US 8,590,535 B2
(45) Date of Patent: Nov. 26, 2013

(54) LARYNX MASK HAVING AN ESOPHAGEAL PASSAGE

(75) Inventor: Werner F. Dubach, Maur (CH)

(73) Assignee: Singularity AG, Maur (CH)

( * ) Notice: Subject to any disclaimer, the term of this patent is extended or adjusted under 35 U.S.C. 154(b) by 198 days.

(21) Appl. No.: 13/130,493

(22) PCT Filed: Nov. 20, 2009

(86) PCT No.: PCT/CH2009/000373
§ 371 (c)(1),
(2), (4) Date: May 20, 2011

(87) PCT Pub. No.: WO2010/060226
PCT Pub. Date: Jun. 3, 2010

(65) Prior Publication Data
US 2011/0220117 A1    Sep. 15, 2011

(30) Foreign Application Priority Data

Nov. 27, 2008  (CH) .................................... 1859/08

(51) Int. Cl.
*A61M 16/00*  (2006.01)
*A61M 16/04*  (2006.01)

(52) U.S. Cl.
USPC ............. 128/207.15; 128/207.14; 128/200.26

(58) Field of Classification Search
USPC ........... 128/200.26, 207.14–207.16; 604/268, 604/524, 528, 541, 543; 600/141–142, 146
See application file for complete search history.

(56) References Cited

U.S. PATENT DOCUMENTS

| 5,878,745 | A | 3/1999 | Brain |
| 7,040,322 | B2 | 5/2006 | Fortuna |
| 7,305,985 | B2 * | 12/2007 | Brain ....................... 128/200.26 |
| 7,506,648 | B2 * | 3/2009 | Brain ....................... 128/207.15 |
| 2003/0037790 | A1 | 2/2003 | Brain |
| 2006/0151039 | A1 * | 7/2006 | Reinhard et al. ............. 138/112 |
| 2006/0180156 | A1 * | 8/2006 | Baska ....................... 128/207.15 |
| 2010/0059061 | A1 * | 3/2010 | Brain ....................... 128/207.14 |
| 2010/0242957 | A1 * | 9/2010 | Fortuna ..................... 128/202.22 |

FOREIGN PATENT DOCUMENTS

| EP | 1875937 A2 | 1/2008 |
| GB | 2404863 A1 | 2/2005 |
| WO | 2005011784 A1 | 2/2005 |
| WO | 2006125986 A | 11/2006 |

OTHER PUBLICATIONS

Deltona Innovations AG., "International Preliminary Report on Patentability," PCT International Application No. PCT/CH2009/000373 filed Nov. 20, 2009 (May 31, 2011).

* cited by examiner

*Primary Examiner* — Clinton T Ostrup
*Assistant Examiner* — Douglas Sul
(74) *Attorney, Agent, or Firm* — Janet Sleath; Speckman Law Group PLLC

(57) ABSTRACT

A larynx mask (1) includes a cover plate (12) having a peripheral cull (13) adjoining thereon and is provided with a tube insertion connector (11) at the proximal end, while the tip (4) has a special design at the distal end. The cover plate 12 ends in the region of the tip on the cuff, or even before that, and the esophageal passage (18) runs as an open channel (20) over a constricted region (13') of the cuff (13). Said channel preferably includes a widening (22) and is delimited on both sides by reinforcement means (21), which are preferably formed by reinforcing walls (21') or additionally as reinforcing ribs (21"). Said design of the lead-through of the esophageal passage results in a considerable reinforcement of the proximal tip of the larynx mask and therefore counteracts possible kinking of the tip (4).

10 Claims, 4 Drawing Sheets

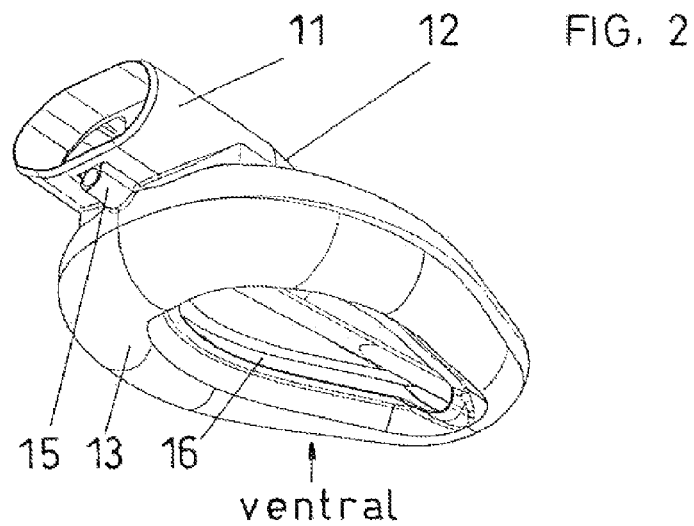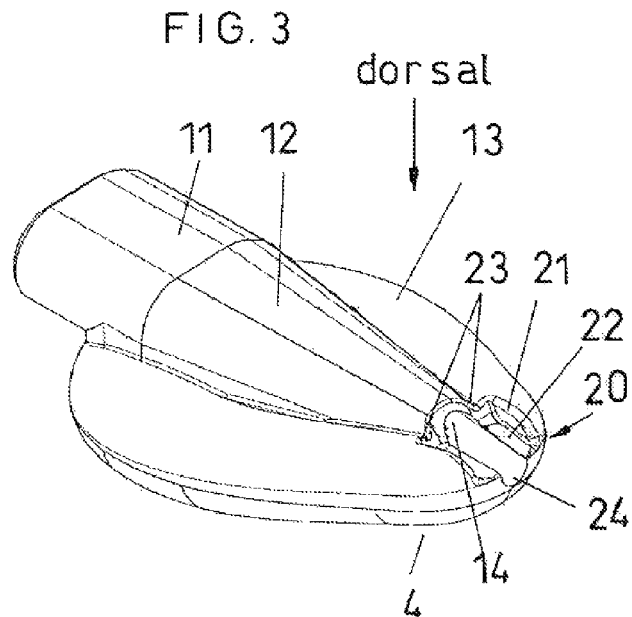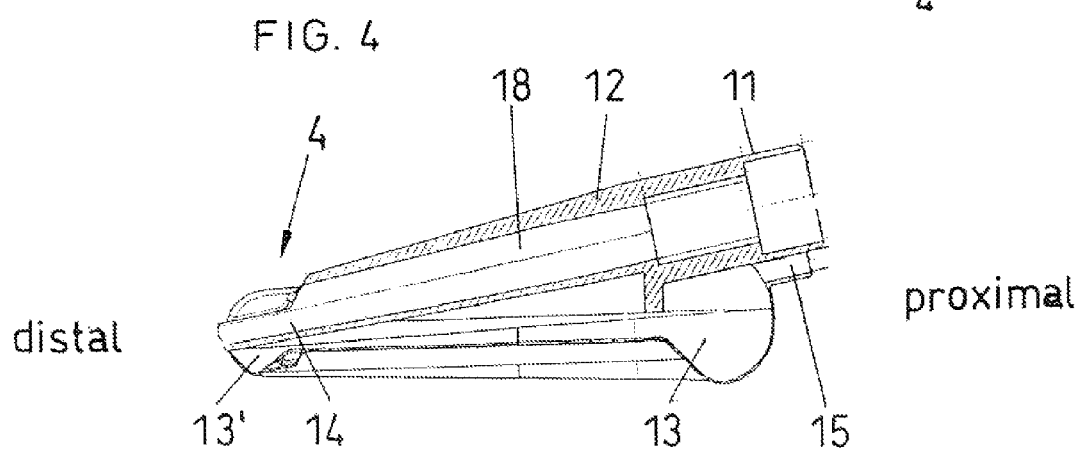

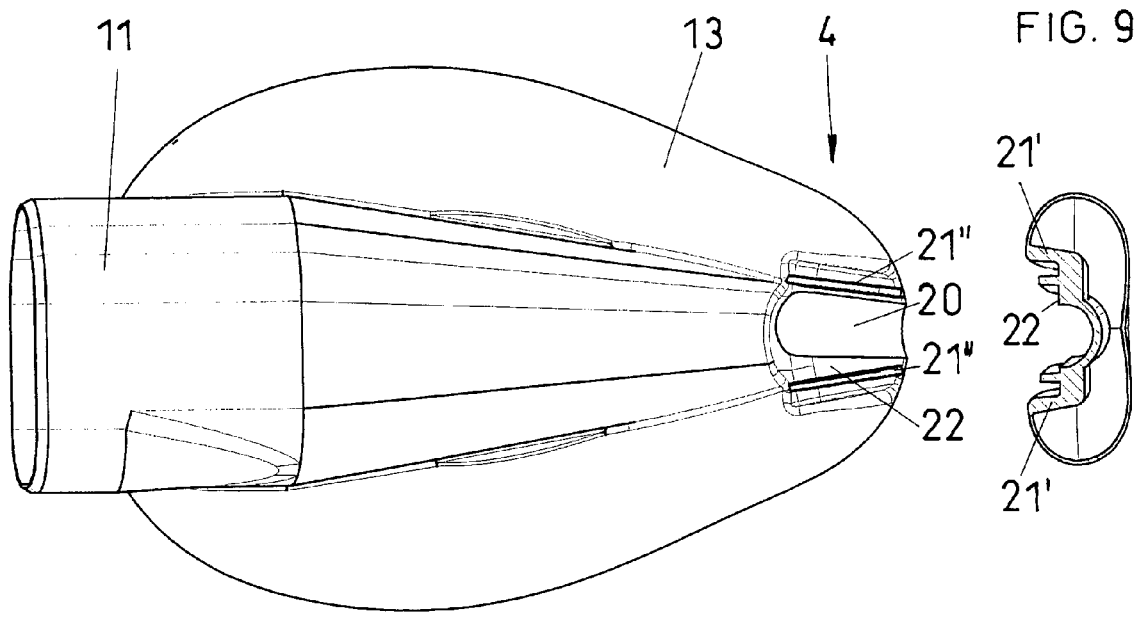
FIG. 8
FIG. 9
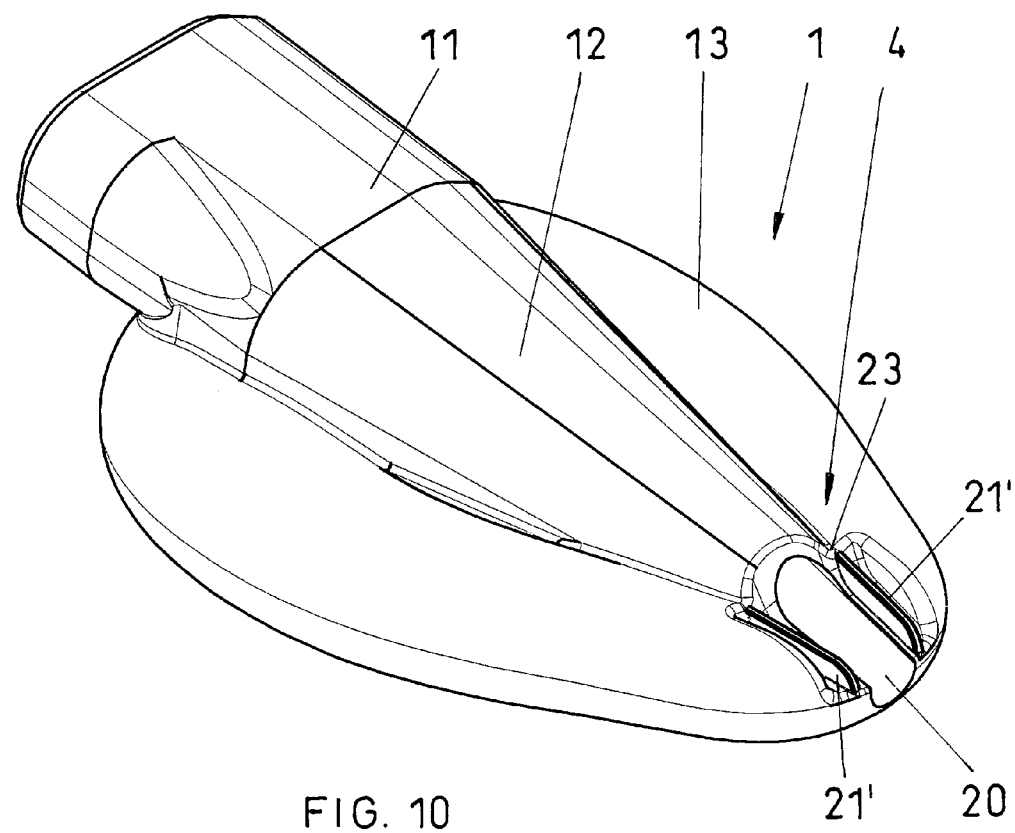
FIG. 10

LARYNX MASK HAVING AN ESOPHAGEAL PASSAGE

This application is the US national phase entry of International Patent Application no. PCT/CH2009/000373, filed Nov. 20, 2009, which claims priority to Swiss patent application no. 1859/08 filed Nov. 27, 2008.

FIELD OF THE INVENTION

The present invention relates to a larynx mask, suitable for insertion through the middle of the pharynx via the epiglottis, comprising a cover plate with a tube insertion connector, a respiration lumen opening and an oesophageal passage as well as an inflatable cuff peripherally surrounding the cover plate on the ventral side.

BACKGROUND

Larynx masks are supplied with supraglottic tubes which are inserted into the pharynx of a patient to keep the airways open and to ventilate the patient. By means of the supraglottic tube a larynx mask is inserted through the middle of the pharynx via the epiglottis into the lower pharynx and positioned behind or around the larynx. Such larynx masks are used to ventilate a patient while he/she is anaesthetised. They also allow the introduction of tubes, probes, optical instruments and other instruments into the airways. More and more frequently such larynx masks have oesophageal access. This allows the introduction of probes into the oesophagus and the stomach in order to remove gastric juices and other fluids as well as air from the stomach. In anaesthetised patients emptying of the stomach is intended to prevent the stomach contents flowing back into the upper respiratory tract and being aspirated into the unprotected airways (windpipe, bronchi and lungs). A further advantage of an oesophageal access is the removal of passively or actively regurgitated stomach contents from the upper oesophagus to outside, which thereby represents limited, and thus inadequate, aspiration protection. However, these larynx masks do not allow the removal of fluids from the pharynx.

A large number of different larynx masks are known on the market. A typical example is set out in U.S. Pat. No. 5,878,745. This shows a gastro-laryngeal mask in which the supraglottic tube is a pipe through which several tubes can be fed. These tubes have lumens which are used for ventilation and for an oesophageal access.

Inserting a larynx mask is not always easy. Larynx marks with a relatively rigid supraglottic tube can be introduced more easily, whereby their rigidity prevents adaptation of the position of the larynx mask to the anatomical conditions. Insertion into the pharyngeal cavity by means of a relatively rigid supraglottic tube can result in injury, and positioning in the pharyngeal cavity is not always reliable.

Highly flexible larynx masks with corresponding highly flexible supraglottic tubes allow better positioning in the larynx but are more difficult and therefore occasionally more traumatic to insert and more difficult to position in the pharynx. Accordingly, it often happens that when inserting such highly flexible larynx masks the distal end of the larynx mask, known as the tip, is bent over. This means that reliable sealing of the larynx mask is no longer present. To remedy this problem a more rigid material can be resorted to, whereby, however, the advantages of the highly flexible materials are lost. The result is traumatic effects in the central pharyngeal cavity. Even with a slightly increased air pressure in the cuff this problem cannot always reliably be solved. In the larynx masks known today, the oesophageal passage always passes through the cuff. This complicates the entire manufacturing of the larynx mask. If kinking or even just slightly greater bending of the tip of the larynx mask occurs the oesophageal passage is mostly then no longer free and an instrument or a tube can no longer be passed through.

A number of larynx masks with an oesophageal passage are known. The oesophageal passage ends in an oesophageal outlet on the extreme distal end of the larynx mask. The oesophageal passage now has to pass through the circumferential sealing area of the larynx mask. If a larynx mask is a version without an inflatable cuff, as set out in documents EP 1 875 937 or GB 2 404 863, this is relatively unproblematic as the larynx mask is overall designed much more rigidly and in practice kinking of the tip does not constitute a relevant problem.

Considerably more complex is the situation in the case of larynx masks with an inflatable cuff. On the one hand due to the thin wall of the cuff the tip of the larynx mask is very flexible and therefore susceptible to kinking, and on the other hand passing the oesophageal passage through the cuff is very problematic. This problem of passing through the cuff is solved by WO 2006/125 986 with a complex four-part larynx mask and a separate tube as the oesophageal passage which can subsequently be pushed through the cover plate and the tracheal tube.

A similar design in disclosed in US 2004/0020491. Additionally here the passed through separate tube of the oesophageal passage is sealed with a separate cuff.

Although the solution with a separate tube as the oesophageal passage reinforces the larynx mask overall, so that the risk of kinking of the tip is reduced, it makes the entire design larger and less manageable. This also applies to the solution in accordance with U.S. Pat. No. 5,878,745.

Finally a larynx mask is known from US 2003/0037790 with an inflatable cuff whereby where the closed oesophageal passage is passed enclosed over the cuff and the outlet lies at the proximal end of the tip on the other side of the inflatable cuff. The closed course, with multiple bends, makes use of the oesophageal passage for instrumentation practically impossible.

SUMMARY

It is therefore the aim of the present invention to improve a larynx mask in such a way that when using a highly flexible material said problems no longer occur, or their occurrence is greatly reduced, and also allow regurgitated food and liquids to pass into the dorsal pharynx. In addition improved use of the oesophageal passage for instrumentation should be made possible.

This aim is achieved by a larynx mask suitable for insertion through the middle of the pharynx via the epiglottis, comprising a cover plate with a tube insertion connector, a respiration lumen opening and an oesophageal passage as well as an inflatable cuff peripherally surrounding the cover plate on the ventral side, whereby the cover plate extends proximally over the cuff, wherein the oesophageal passage emerges at the proximal end of the cover plate on the dorsal side and is passed over the cuff as an open channel, whereby reinforcing means acting on both sides of this channel and in the axial direction of the channel are present which counteract possible kinking of the proximal tip of the larynx mask.

Other advantageous embodiments are set out in the dependent claims and their relevance and action mechanism are explained in the following description with reference to the attached drawings.

BRIEF DESCRIPTION OF THE DRAWINGS

The drawings show two preferred variants of the subject matter of the invention, with FIGS. 1 to 7 showing a first embodiment and FIGS. 8 to 10 showing a second embodiment.

FIG. 2 shows a ventral distal view of the larynx mask and

FIG. 3 again shows a perspective view, but seen from the dorsal proximal side.

FIG. 4 shows a diametric longitudinal section through the larynx mask in which

FIG. 8 shows a second embodiment of the larynx mask with a view towards the dorsal side, while FIG. 9 shows a vertical section through the larynx mask in the area of its top. Finally FIG. 10 again shows a perspective view of the second embodiment of the larynx mask.

DETAILED DESCRIPTION

Figure 1:
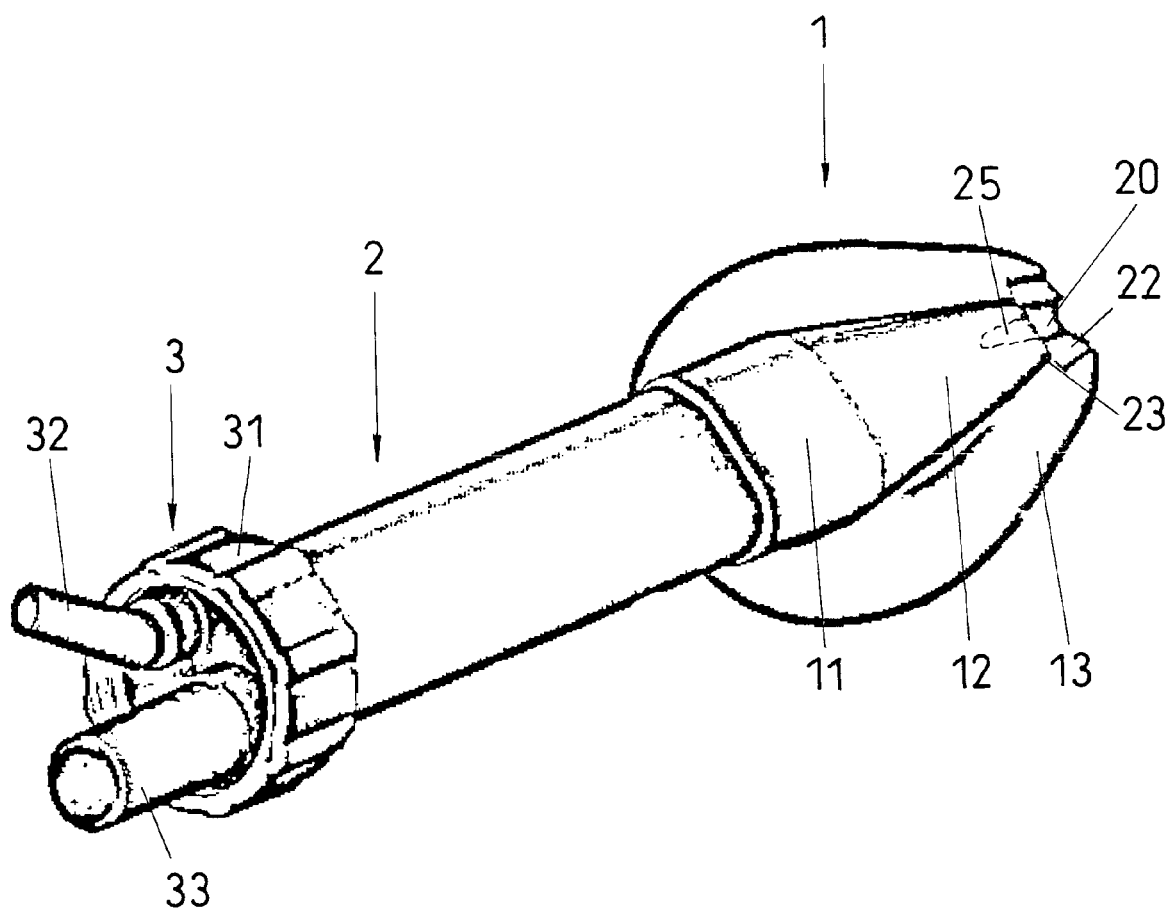
FIG. 1 shows a perspective overall view of the larynx mask in accordance with the invention with a connected supraglottic tube with a connecting connection.

In FIG. 1, the larynx mask 1 with a connected supraglottic tube 2 can be seen, whereas at the other end a connecting connector 3 is attached. To connect the larynx mask 1 with the supraglottic tube 2, the larynx mask has a tube insertion connector 11 at the distal end.

This tube insertion connector 11 is connected in one piece to the directly adjoining cover plate 12, on which, again in one piece, an inflatable collar, known as the cuff 13 is formed and completely surrounds the cover plate 12 on its ventral periphery. The supraglottic tube 2 can contain two tubes or as here can preferably be provided with two separate lumens. One lumen is used as a respiration lumen, while the other lumen is designed as an instrument or oesophageal lumen. In between a third lumen may be present by means of which the bends of the supraglottic tube can be changed by means of appropriate tension and pressure means arranged therein. However, in FIG. 1 the supraglottic tube is shown in a straight initial position. The adjustability or change in the bend of the supraglottic tube 2 can be affected by turning an adjusting ring 31. Projecting from the connecting connector 3 is an oesophageal inlet connector 32 and a respiration inlet connector 33. With regard to the features of larynx mask 1, reference is made to the following figures.

In FIG. 2 the larynx mask 1 is shown perspectively in a view from ventral-distal. Here the tube insertion connector 11 can be recognised and the inside can be partially seen so that a partial view into the oesophageal passage 18 is evident. In all the figures the larynx mask 1 is shown as it comes out of an appropriate plastic injection mould. Here, the inner edge of the cuff 13 is not yet connected to an internal circumferential adhesive wall 16. Although an adhesive wall 16 is mentioned here, the connection of the edge of the cuff 13 to the adhesive wall 16 can not only take place through adhesion but also through welding. More particularly, ultrasonic welding could be considered here. Through the elasticity of the material the shape of the cuff 13 is practically the same as if it were already filled with air. For supplying the filling air into the cuff 13, a ventilation connection 15 that opens directly into the cuff 13 is provided under the tube insertion connector 11, as can most clearly be seen in the vertical section in FIG. 4.

Figure 5:
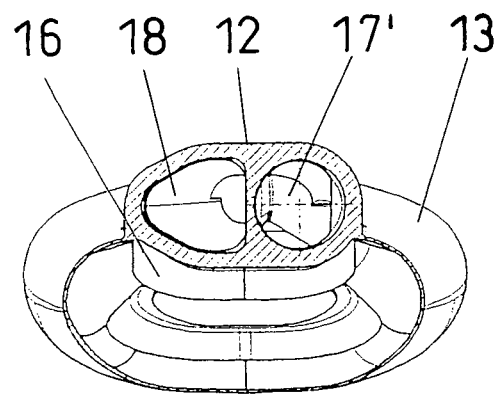
FIG. 5 is a vertical section through the larynx mask in the area close to the tube insertion connection looking towards the distal end.

Within the cover plate 12, in the area close to the tube insertion connector 11 the respiration lumen is initially still completely closed in cross-section as is the lumen of the oesophageal passage 18. Accordingly the respiration lumen is designated 17'. The vertical section in accordance with FIG. 5 is shown looking towards the tip 4 and/or the distal end of the larynx mask. Accordingly, when looking into the oesophageal passage 18 the oesophageal outlet 14 can be seen.

Figure 6:
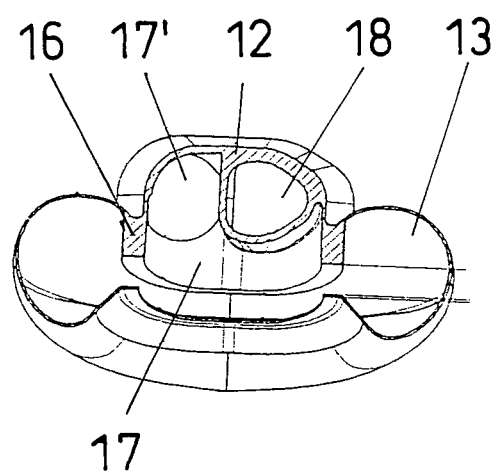
FIG. 6 shows an approximately central cross-section looking towards the proximal end, while FIG. 7 again shows a vertical section close to the distal end of the cover plate looking towards the distal end.
Figure 7:
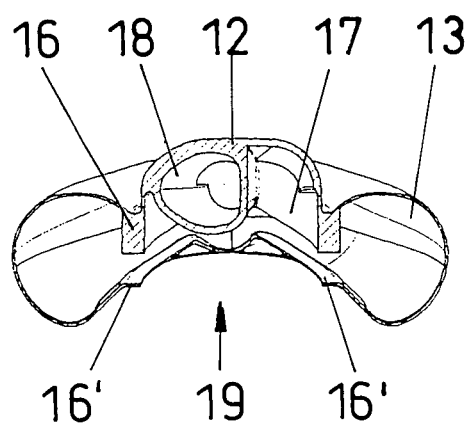

Running from proximal to distal the respiration lumen 17' continuously opens and thus forms the respiration lumen opening 17 and communicates with the sealed respiration chamber 19 lying underneath it which is delimited by the cuff 13. In FIG. 6 the vertical section is shown looking towards the proximal end, so that here free passage of respiration lumen 17' to its outlet in the tube insertion connector 11 can be seen, while the respiration lumen opening 17 can also be seen. FIG. 7 again shows a vertical section, relatively close to the distal end and/or close to the tip 4 of the larynx mask 1, again looking towards the distal end. Again clearly visible are the adhesive wall 16 and the corresponding adhesive edge 16' on the cuff 13, which is here not yet connected to the adhesive wall 16.

The oesophageal passage 18 running laterally ventrally next to the respiration lumen opening 17 helps on the one hand to reinforce the larynx mask in the axial direction in order to prevent or reduce kinking in the middle area of the mask, and on the other hand the oesophageal passage 18 on the ventral side helps to keep the epiglottis away from the respiration lumen opening 17.

Preferably the larynx mask also has a proximally closed sack-like lumen between the oesophageal passage 18 and respiration lumen 17' and respiration lumen opening 17 which allows the use of a longitudinal reinforcing element.

The distal end of the larynx mask 1 forms its tip 4. In the area of the tip 4 which forms part of the cover plate 12, the oesophageal passage 18 which runs closed through the cover plate 12 opens into oesophageal outlet 14. The oesophageal passage 18 then passes over cuff 15 as a dorsally open channel 20. The cross-section of this channel 20 is shown here as a half-cylinder. Correspondingly the cuff 13 is reduced in cross-section in the area of the tip 4 as the cover plate 12 runs deeper here in the ventral direction. The reduced cross-section area of the cuff 13 is designated 13'. In principle the cross-section of the cuff can be reduced to zero in this area so that the cuff is discontinuous in the area of the tip. However, the shown solution is preferred due to the better seal to the epiglottis. In principle the delimiting walls to the cuff 13 can run directly adjacent on the semi-cylindrical open channel 20. The delimiting walls are in principle designed as reinforcing means 21 for the cover plate 12. Irrespective of whether these walls are or are not reinforced or thickened in cross-section, they only work as a reinforcement through their direction perpendicular to the possible direction of kinking. This also applies if these walls are arranged directly adjacent to the open channel 20.

Preferably, however, these reinforcing walls 21' are applied as reinforcing means 21 opposite the open channel 20 with its channel base 24 laterally offset. This lateral offsetting forms a channel widening 22 in the form of intermediate bases. Although it would also be possible to reinforce these intermediate bases with appropriate material thickening this has little effect in the sense of preventing kinking of the tip 4.

Through the offsetting of the reinforcing walls 21', laterally in the transition area of the cover plate 12 to the cuff 13, at the proximal end of this widened area an escape point 23 is practically formed on both sides. If in the event of regurgitation of the stomach contents these cannot be taken up by the oesophageal passage alone within a sufficient period of time, at the dorsal escape points 23 these stomach contents can also escape dorsally of the cuff into the pharynx, without the risk of the material entering the respiration area ventrally through the cuff. In addition, pharyngeal fluid can accumulate in the area of the open channel 20 which can be removed through the oesophageal passage directly or by way of suction with a tube.

In a further preferred embodiment the reinforcing walls 21' can extend proximally along the dorsal inner side of the cuff only in the cuff tip area, so that the escape of stomach contents dorsally is even more efficient and not only the cuff tip but also the proximal cuff are protected against kinking.

In another preferred embodiment the oesophageal outlet 13 can be even further to proximal, so that the open channels 22, 24 are not only limited to passing over the cuff tip. This allows even more efficient escaping of regurgitated stomach contents to dorsal in the pharynx and easier removal by suction of collected pharyngeal secretion. This widened suction opening is designated 25 and is added as a broken line in FIG. 1.

The widened channel also has the advantage that an instrument or a probe or an optical device that is passed through the oesophageal passage can take on the required curvature early on in order to be introduced as required into the oesophagus. If an oesophageal passage is passed through the cuff, as is the case in the best known solutions in the prior art, the outlet point in the ventral direction is moved further to ventral and, accordingly, in certain circumstances the required handling ability may be made more difficult.

With the reduced cuff tip with an open channel, a wedge-shaping of the larynx mask in the upper oesophageal inlet is deliberately dispensed with. In addition to the above advantages this also has the benefit that the naso-oesophageal or naso-gastric access allows appropriate instrumentation or the insertion of temporary or permanent tubes.

As an additional possibility of reinforcing the tip 4 of the larynx mask 1 another solution is shown in FIGS. 8 to 10. As the oesophageal passage does not run exactly centrically in the longitudinal direction, its extension, namely the open channel 20, also does not run centrically but slightly from lateral to towards the center. The channel widening 22 can also be seen in the solution shown here. In addition, here, on the channel widening 22, which here is also in the form of a thickened wall section, reinforcing ribs 21" running parallel to the wall 21' are additionally applied on the channel widening 22 between the first reinforcing means of the reinforcing walls 21'. This achieves optimum reinforcement against the kinking effect. Nevertheless it is still ensured that stomach contents can escape.

The larynx mask in accordance with the invention therefore on the one hand provides greater security for the anaesthetist against possible kinking of the tip 4 of the larynx mask as a result of which he can work more quickly and reliably, and at the same time provides improved access to the oesophagus thanks to the oesophageal outlet 14 which is in the proximal direction earlier, thereby achieving greater mobility of the instruments, tubes or optical system being passed through the oesophageal passage.

LIST OF REFERENCE NUMBERS

1. Larynx mask
2. Supraglottic tube
3. Connecting connector
4. Tip of a larynx mask
11. Tube insertion connector
12. Cover plate
13. Cuff
13'. Cuff in the area of the tip
14. Oesophageal outlet
15. Ventilation connection of the cuff
16. Adhesive wall
16'. Adhesive edge
17. Respiration lumen opening
17'. Respiration lumen
18. Oesophageal passage
19. Sealed respiration chamber
20. Open channel
21. Reinforcing means
21'. Reinforcing walls
21" Reinforcing ribs
22. Channel enlargement
23. Escape points
24. Base of the channel
25. Widened suction opening
31. Adjusting ring
32. Oesophageal inlet connector
33. Respiration inlet connector

The invention claimed is:

1. A larynx mask suitable for insertion through the middle of the pharynx via the epiglottis, comprising:
   (a) a cover plate with a tube insertion connector, a respiration lumen opening, and an oesophageal passage; and
   (b) an inflatable cuff peripherally surrounding the cover plate on a ventral side of the cover plate, wherein the cover plate extends distally over the cuff,
   wherein the oesophageal passage emerges from the cover plate before a distal end of the cover plate on a dorsal side of the cover plate and passes over the cuff as an open channel in the cover plate, and wherein reinforcing means are provided on both sides of the open channel that act approximately parallel to a longitudinal axis of the open channel and thereby counteract possible kinking of a distal tip of the larynx mask;
   (c) reinforcing walls running ventro-dorsally on each side of the open channel, whereby the distal tip of the larynx mask is reinforced against kinking;
   wherein the reinforcing walls are arranged parallel to the open channel and are offset by a distance from the open channel, and a channel widening in the form of an offset projection is provided between the open channel and the reinforcing walls on each side of the open channel.

2. The larynx mask of claim 1 wherein at the distal tip of the larynx mask, a cross-section of the cuff is reduced by the depth of the open channel.

3. The larynx mask of claim 2 wherein a base of the open channel is formed by a ventral area of the oesophageal passage.

4. The larynx mask of claim 1, wherein the cuff is discontinuous at the distal tip of the larynx mask.

5. The larynx mask of claim 1 wherein the reinforcing walls are thicker than areas of the cuff that adjoin the reinforcing walls.

6. The larynx mask of claim 1 wherein at least one reinforcing rib is formed on the offset projection.

7. The larynx mask of claim 1 wherein the depth of the open channel is at least one to two thirds of a diameter of the oesophageal passage.

8. The larynx mask of claim 1 wherein escape points are formed at a transition of the cuff to the cover plate at a proximal end of the channel widening, wherein the escape points are configured such that stomach contents are able to escape into the pharynx.

9. The larynx mask of claim 1 wherein the reinforcing walls are continued along a dorsal inner side of the cuff on both sides of a distal tip of the cuff.

10. The larynx mask of claim 1 wherein the oesophageal passage is open in a distal area of the cover plate and thereby forms an enlarged suction opening.

* * * * *